US 6,250,303 B1

(12) United States Patent
Delaney

(10) Patent No.: US 6,250,303 B1
(45) Date of Patent: Jun. 26, 2001

(54) MALE CONDOM

(76) Inventor: Gregory Patrick Delaney, Keepers Farms, Banbury Road, Pillerton Priors, Warwickshire CV35 OPA (GB)

( * ) Notice: Subject to any disclaimer, the term of this patent is extended or adjusted under 35 U.S.C. 154(b) by 0 days.

(21) Appl. No.: 09/308,939

(22) PCT Filed: Nov. 27, 1997

(86) PCT No.: PCT/GB97/03249

§ 371 Date: Jul. 26, 1999

§ 102(e) Date: Jul. 26, 1999

(87) PCT Pub. No.: WO98/23234

PCT Pub. Date: Jun. 4, 1998

(30) Foreign Application Priority Data

Nov. 27, 1996 (GB) .................................................. 9624573

(51) Int. Cl.[7] .................................................. A61F 6/04
(52) U.S. Cl. .......................................... 128/844; 128/918
(58) Field of Search .................................... 128/842, 844, 128/918; 604/347–353

(56) References Cited

U.S. PATENT DOCUMENTS 2,433,538   12/1947   Warner .
3,648,700   3/1972   Warner .
4,820,290   4/1989   Yahr .
4,846,197   7/1989   Benjamin .
5,333,621 * 8/1994   Denzer ................................. 128/844
5,361,779 * 11/1994  Wilson ................................. 128/844
5,513,652 * 5/1996   Schwartz ............................. 128/844
5,579,784 * 12/1996  Harari ................................. 128/844

FOREIGN PATENT DOCUMENTS 663151   11/1987   (CH) .
641521    8/1928   (FR) .
2509606   1/1983   (FR) .
9420052   9/1994   (WO) .

* cited by examiner

Primary Examiner—Michael A. Brown
(74) Attorney, Agent, or Firm—Wood, Phillips, VanSanten, Clark & Mortimer

(57) ABSTRACT

A male condom having a flexible sheath to receive the glans of the penis and a wide elastomeric belt to lie around and grip the penis immediately behind the glans. A part of the penis behind the belt is left bare while on the other hand one or two elements connect the elastomeric belt to another belt intended to lie around the base of the penis.

23 Claims, 5 Drawing Sheets

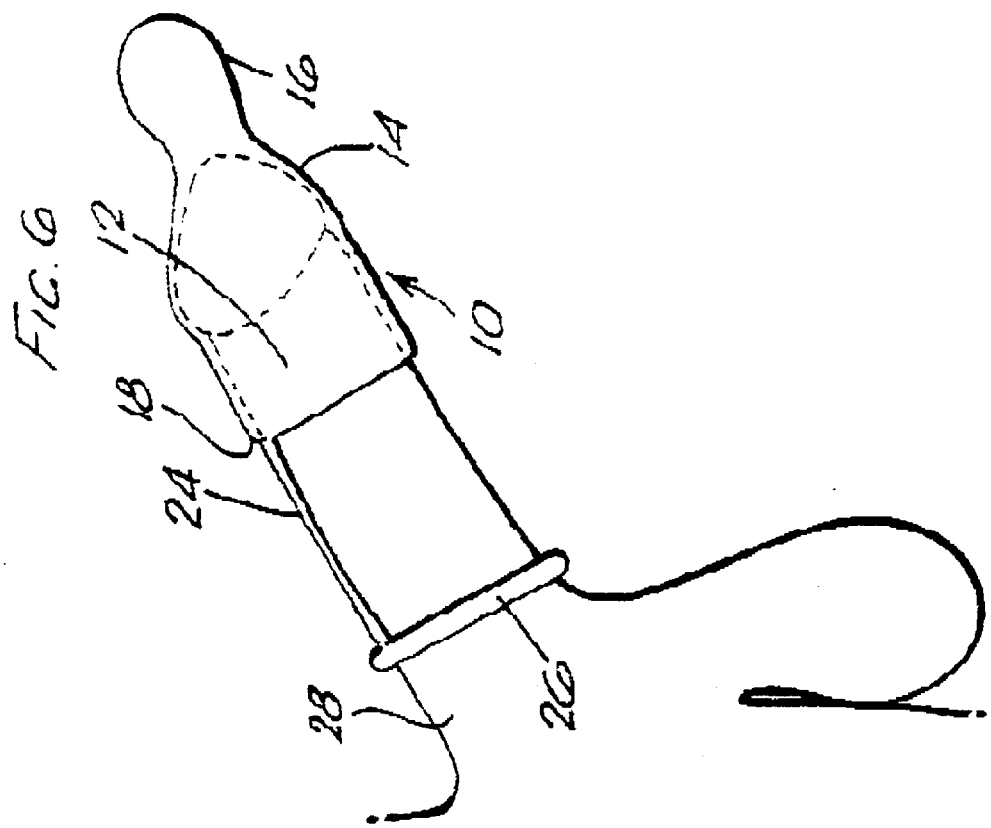
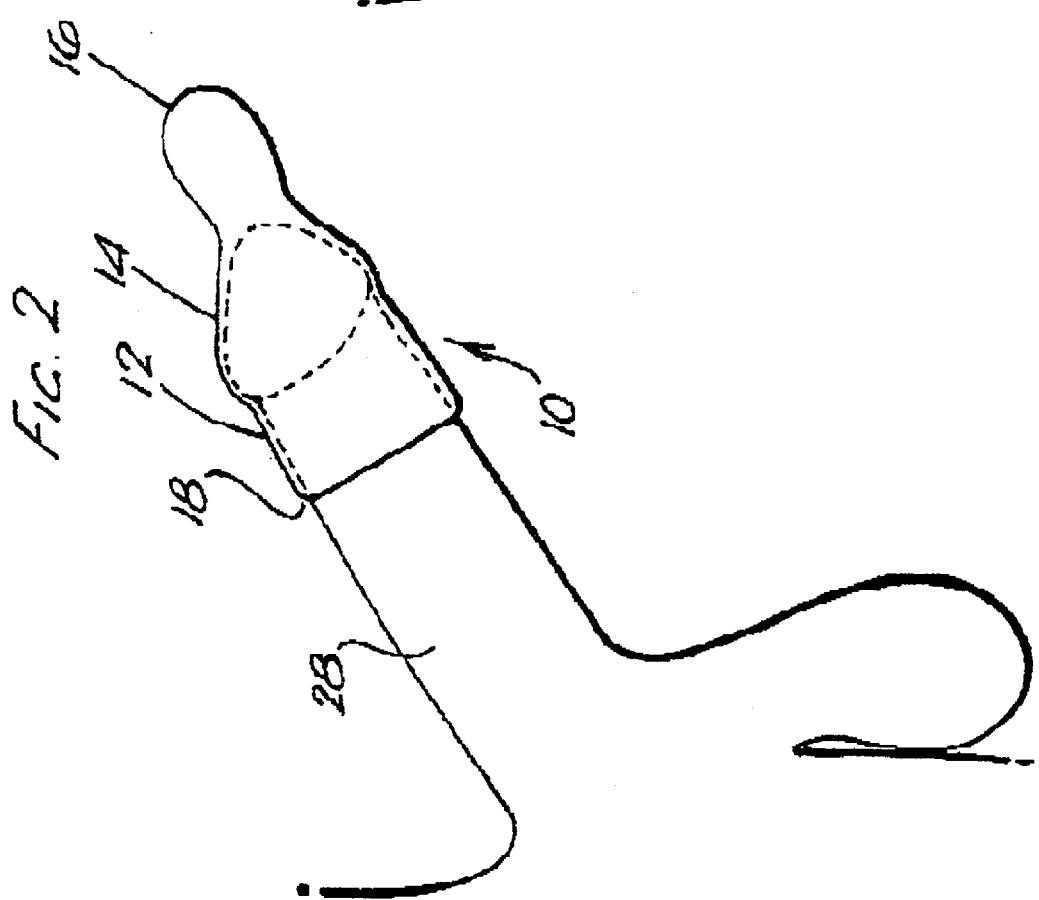

MALE CONDOM

The invention relates to a male condom.

The known male condom comprises a flexible sheath which is rolled onto the penis to cover the entire length of the penis to the base thereof. One reason why men may not be willing to use the known male condom is that it reduces the sensation that they feel during sexual intercourse. In particular, the condom reduces or eliminates the sense of touch on the surface of the penis.

According to the invention there is provided a male condom comprising a flexible resilient sheath to receive the glans of the penis and a wide elastomeric belt to lie around and grip the penis immediately behind the glans leaving the majority of that length of penis which is behind the glans bare.

A man wearing the condom according to the invention will thus have heightened sensation during intercourse compared with the known condom as all or the majority of the shaft of the penis is bare. At the same time, the wide elastomeric belt gripping the penis behind the glans will ensure that sperm do not escape backwards past the belt so that the contraceptive and prophylactic qualities of the condom according to the invention are the equal of the known condom. The condom of the invention is designed by the resilience of the sheath and the grip of the belt, such that it cannot be pulled off an erect penis. The grip of the belt is preferably such as to prevent gas or liquid entry to the sheath in use. Thus any force on the sheath to remove the condom will stretch the resilient sheath thus increasing the vacuum within the sheath and hence increasing the opposing force acting to keep the condom on. The inherent reaction force acting to keep the condom on makes it very safe. The belt preferably smoothly tapers to its rear edge. This also reduces any force acting to pull the condom off.

The belt is preferably so stiff that it cannot be rolled in use. This also reduces the possibility of removal of the condom. The belt may be arranged to be manually reversed by a user when putting on the condom. This method is similar to the unrolling method of the known condom.

The belt may be of any suitable width and may be less than 60 mm wide, preferably less than 25 mm wide and most preferably less than 12 mm wide. Clearly a balance is to be struck between the elastic force of the belt, in acting effectively to prevent semen passing through the belt, and its width. While a narrow belt is desirable from the point of view of sensation as more of the penis is bare, the comfort of the user must also be considered and the increased elastic strength of the belt may make the condom less comfortable to wear. A compromise should be adopted.

The wide elastomeric belt may be arranged to be in direct contact with the skin of the penis, but alternatively at least part of the axial length of the belt is lined with absorbent material. The absorbent material may take any suitable form and may be for example neoprene. The absorbent material preferably contains a contraceptive or prophylactic substance such as spermicide and may also contain a substance with a pleasant fragrance.

The belt is preferably shaped at its forward end to the shape of the coronal sulcus. Thus the forward edge of the belt is preferably smoothly curved forward to the underside of the condom to a rounded point. This gives a very good fit around the narrowest part of the penis to prevent semen from passing back beyond the belt. The rear edge of the belt may be in a simple circle so that the belt is wider on the underside of the condom than on the top. A restriction is preferably provided at the forward edge of the belt to further improve the fit and to increase the elastic force in that region.

Preferably, the condom is arranged such that the underside of the penis can be left bare in use.

The condom in one embodiment leaves the part of the shaft of the penis behind the wide belt entirely bare. In another embodiment the condom includes a further belt to lie around the base of the penis in use and at least one element connecting the two belts. This provides additional security against the condom being pulled off. The or each element may take any suitable form and may taper from each belt to a central region of the element. In one embodiment the condom includes a single element and in another embodiment the condom includes two oppositely disposed elements.

The part of the condom which is in contact with the shaft of the penis may include forwardly and inwardly directed projections. These will act to resist pulling off of the condom as well as producing a tighter elastic force if the condom should move forwards. The projections are preferably in the form of at least one circumferential band. The projections are preferably in the form of at least one circumferential band so as to form a barrier in addition to providing the other functions described.

The part of the condom which is in contact with the shaft of the penis may additionally or alternatively include suckers to hold the condom onto the penis. As these will inevitably leave a fluid flow path around themselves, means to provide a fluid tight seal will need to be provided behind them.

The condom may include a teat which may be resilient to resist collapse. Thus, the wall of the condom teat may be thicker than the wall of the part of the condom which is arranged to receive the glans of the penis. In this way, the condom will resist the tendency for collapse of the teat to drive semen ejaculated into the condom back towards the elastomeric belt.

Three embodiments of the invention will now be described by way of example and with reference to the accompanying drawings, in which:

FIG. 2 is a side elevation of the condom of FIG. 1 being worn by a user;

FIG. 6 is a side view of the condom of FIG. 4 being worn by a user;

Figure 1:
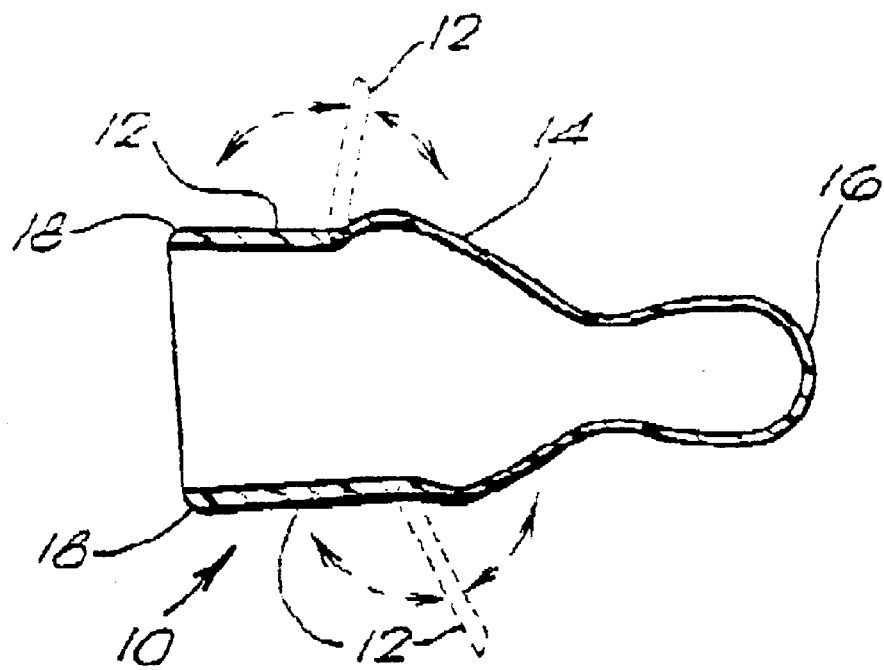
FIG. 1 is a side elevational in cross-section of the condom of the first embodiment of the invention.

The condom 10 of the first embodiment comprises a wide elastomeric belt 12, a bulb part 14 to receive the glans of a male penis and a teat 16.

The condom 10 is formed integrally of elastomeric material. The belt 12 is in the form of a cylindrical tube of uniform wall thickness except at the rear edge 18 which is tapered inwardly. The wall thickness of the bulb 14 is thinner, being similar in wall thickness to the wall thickness of the known condom, so that the bulb 14 is highly flexible. There is a smooth transition in the outer wall from the belt 12 to the bulb 14. The bulb 14 leads to the teat 16 at the front of the condom where the wall thickness increases again although not to the same thickness as the wide belt 12. Although the teat 16 is of thicker material than the belt 14, the teat 16 is still flexible, like the bulb 14, but is more resilient to resist collapse. The teat 16 is also larger than on the known condom.

The condom 10 is supplied with the belt 12 folded forwards over the bulb 14 which is itself scrolled inside out. The bulb 14 can thus be rolled onto the end of the penis in the normal way. While the belt 12 is too thick to roll, it can be flipped back onto the shaft of the penis, as shown in dotted lines in FIG. 1, to lie immediately behind the glans as shown in FIG. 2. This leaves the majority of the penis behind the glans bare to allow greater sensation during sexual intercourse. On ejaculation the semen will collect in the teat 16. The increased resilience of the teat 16 will reduce back pressure which otherwise causes semen to be urged back through the bulb 14 towards the wide belt 12. The enlarged size of the teat 16 also reduces this back pressure. The resilience of the thick belt 12 gripping the shaft of the penis also acts to prevent sperm from reaching the rear edge 18 of the condom 10.

The smooth transition in the outer surface of the condom between the teat 16, bulb 14 and belt 12 ensures that there are no raised shoulders which could act either to pull off the condom 10 or to push the condom 10 further onto the penis thus reducing the size of the teat 16 and increasing back pressure. Similarly, the tapered rear edge 18 acts to reduce any force tending to pull off the condom. Any force to pull off the condom will be resisted by stretching of the bulb 14 to cause a pressure decrease in the bulb 14 acting to resist stretching and hence to keep the condom 10 on.

The belt 12 may be 0.5 inch i.e. 12.7 mm long.

Figure 3:
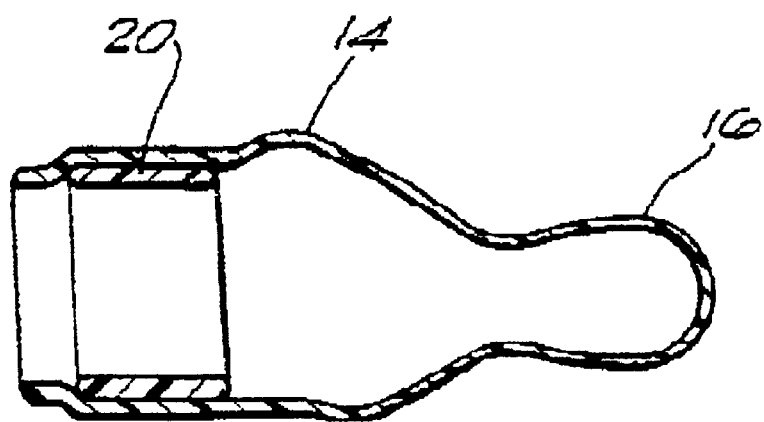
FIG. 3 is a side elevation in cross-section of the condom of the second embodiment of the invention.

FIG. 3 shows the second embodiment which is similar to the first and the same reference numerals will be used for equivalent features. The wide belt 12 is no longer of increased wall thickness but instead has fitted within it a cylindrical tube of resilient absorbent material 20 such as neoprene. The resilient absorbent material 20 may contain contraceptive and/or prophylactic substances such as a known spermicide and may also contain a fragment substance to give the condom a pleasant odour and mask any rubbery odour which it may naturally have. The absorbent resilient material 20 acts as a physical barrier to semen as well as containing substances to act as a chemical barrier to sperm reaching the rear edge 18 of the condom 10.

Figure 4:
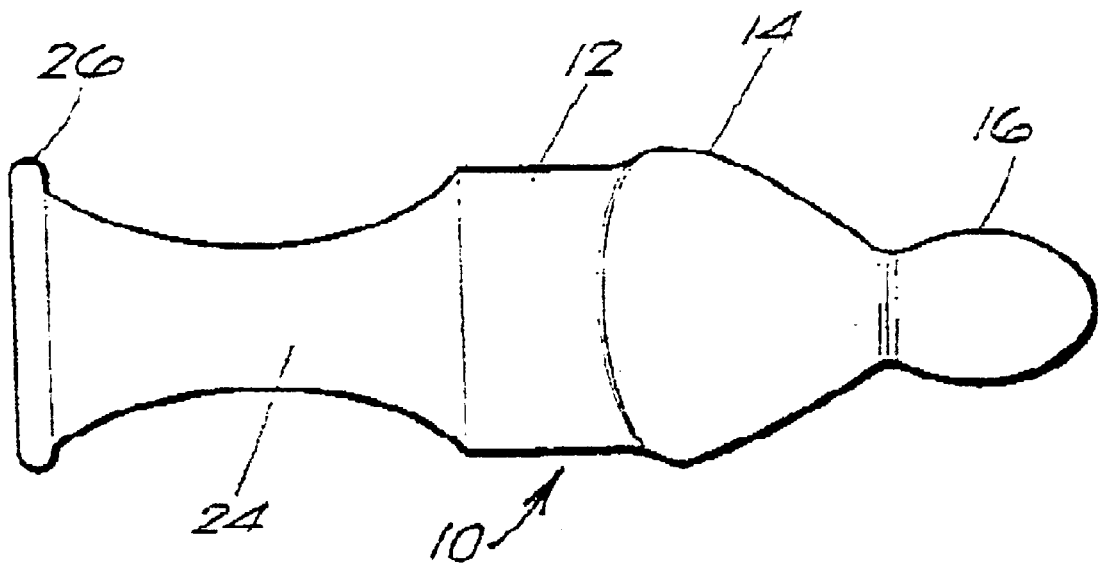
FIG. 4 is a plan view of the condom of the third embodiment of the invention.

FIGS. 4 and 6 show the third embodiment which is again similar to the first embodiment and only the differences from the first embodiment will be described.

In the third embodiment a condom as shown in FIGS. 1 and 2 is provided with an element 24 extending rearwardly from the rear edge 18 of the condom 10. The element 24 extends from a region of about half the circumference of the rear edge 18 and tapers smoothly to a central region from which it widens symmetrically and is connected to a narrow belt 26. The belt 26 and element 24 are formed integrally with the rest of the condom 10.

In use, it is intended that the second belt 26 should lie around the base of the penis, as shown in FIG. 6, as an additional measure to ensure that the condom 10 is not pulled off. It is intended that the element 24 should lie along the top of the penis, as the underside of the shaft of the penis is the most sensitive part of the shaft.

Figure 5:
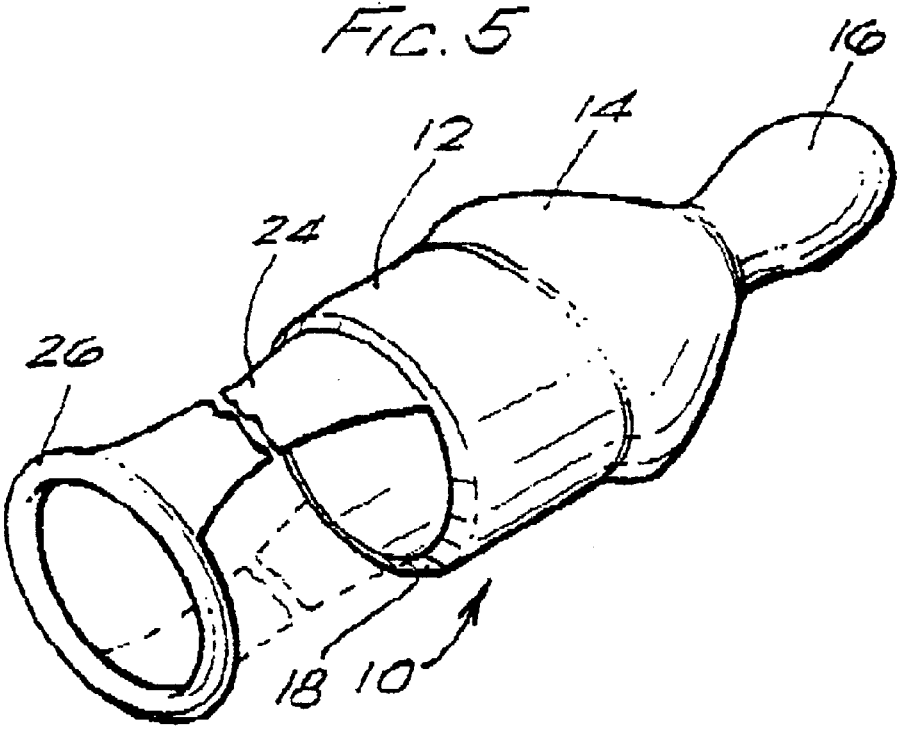
FIG. 5 is a perspective view from one side of the condom of FIG. 4.

In an alternative embodiment, two elements 24 are provided in oppositely disposed positions as shown in dotted lines in FIG. 5. In this case it is intended that the condom should be worn with the elements extending one down each side of the shaft of the penis so that the underside of the penis is still exposed.

Clearly, in a further variant, one or more elements 24 could be connected to the condom of the second embodiment in the same manner, if desired.

While in the embodiments the teat 16 is given additional resilience in comparison with the bulb 14 by increasing the wall thickness, the teat 16 could have the same wall thickness as the bulb 14 for ease of manufacture and its resilience could be increased by an additional treatment such as heat treatment or chemical treatment.

An inwards bead may be provided around the inner edge of the belt 12 to increase grip at that position.

Figure 7:
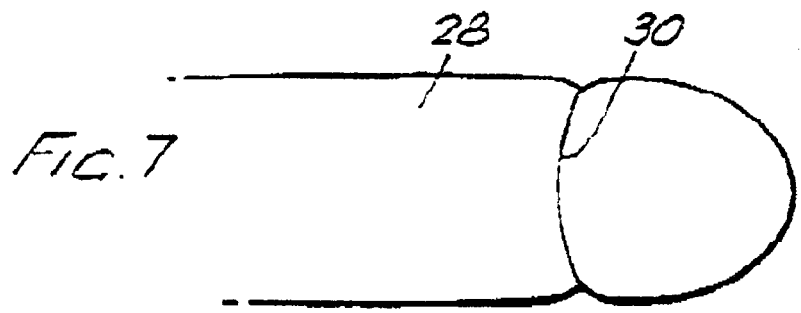
FIG. 7 is a plan view of a penis.
Figure 8:
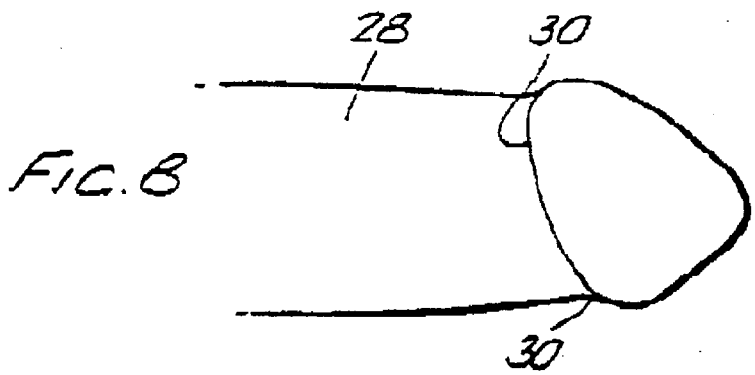
FIG. 8 is a side elevation of a penis.
Figure 9:
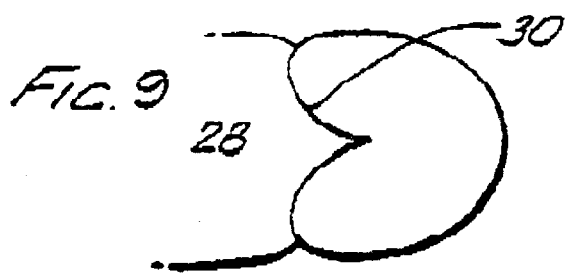
FIG. 9 is an underneath plan view of a penis.
Figure 10:
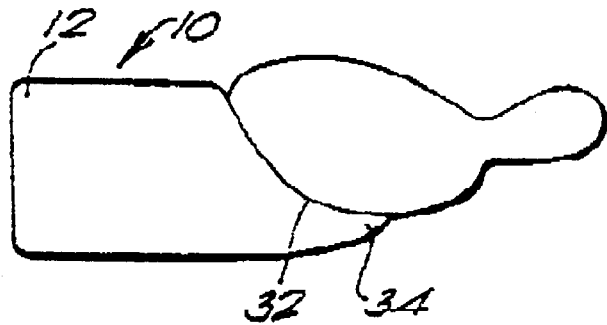
FIG. 10 is a side elevation of the condom of the fifth embodiment.
Figure 11:
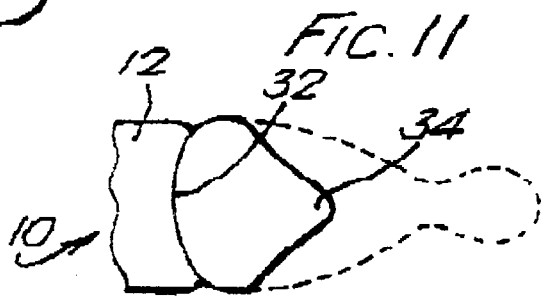
FIG. 11 is a plan view of the belt of the condom of FIG. 10.
Figure 12:
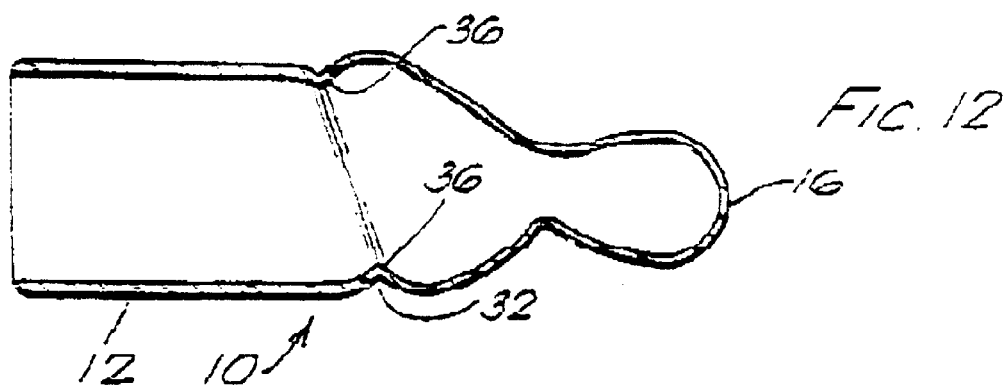
FIG. 12 is a side elevation in cross-section of the condom of FIG. 10.

FIGS. 10, 11 and 12 show the fourth embodiment which is similar to the first embodiment. FIGS. 7, 8 and 9 show a penis 28. The wide belt 12 of the first embodiment was in the form of a cylindrical tube. The wide belt 12 of the fourth embodiment is the same as its rear edge, but at the front edge 32 it is contoured to fit closely into the coronal sulcus 30 of the penis. From the upper side of the condom, the front edge 32 of the wide belt 12 curves smoothly forwards to terminate in a blunt point 34. This provides a much better fit to assist the contraceptive and prophylactic function of the condom, as well as making the condom more comfortable. The condom includes an inwards projection 36 at the front edge 32 of the wide belt 12 to provide an especially tight fit in the coronal sulcus. This has a number of functions and advantages. Firstly, it increases the fluid tightness of the condom at that area. It should be pointed out that while the wide belt is sculpted inwards to follow the tapering shape of the shaft of the penis into the coronal sulcus, the bead 36 provides even greater elastic force in this area. The blood supply to the penis lies towards the centre of the penis, while blood flowing away from the penis is carried in veins on the surface. This bead 36, together with the elastic belt 12 itself, will act to reduce blood flow away from the penis so that greater swelling of the glans results. This acts to deepen the crevice which is the coronal sulcus providing a more tortuous path for any semen and increasing the fluid tightness of the condom. Semen passes through the penis through a duct on the underside. The restriction of the bead 36 may be so tight as to reduce the flow of semen which will improve the contraceptive effectiveness of the condom. The inner surface of the wide belt 12 may be smooth, but alternatively may be roughened to provide frictional resistance to the condom being pulled off. In an alternative embodiment, the inner surface of the wide belt 12 may be coated with an adhesive, which may have a cover sheet. The adhesive will bind the condom to the penis to resist removal of the condom.

Figure 13:
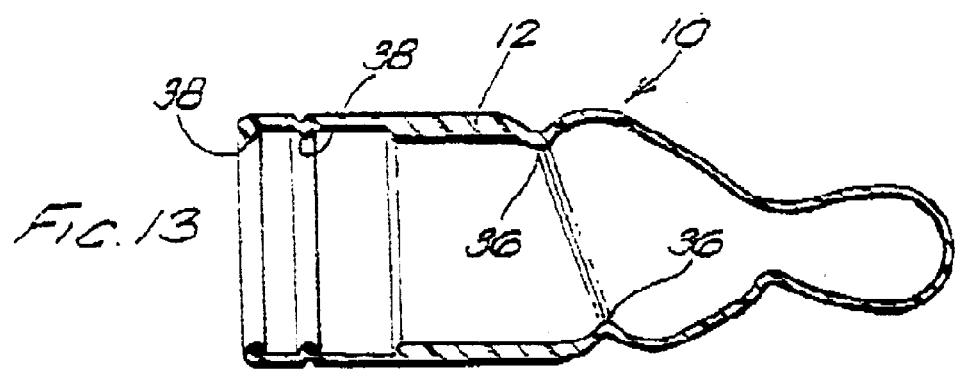
FIG. 13 is a side elevation in cross-section of the condom of the sixth embodiment.

FIG. 13 shows a further embodiment which is similar to the fifth embodiment and in which an additional section to the rear of the wide belt 12 includes two spaced tightness bands 28 of reduced diameter. These will provide a further barrier to escape of semen.

Figure 14:
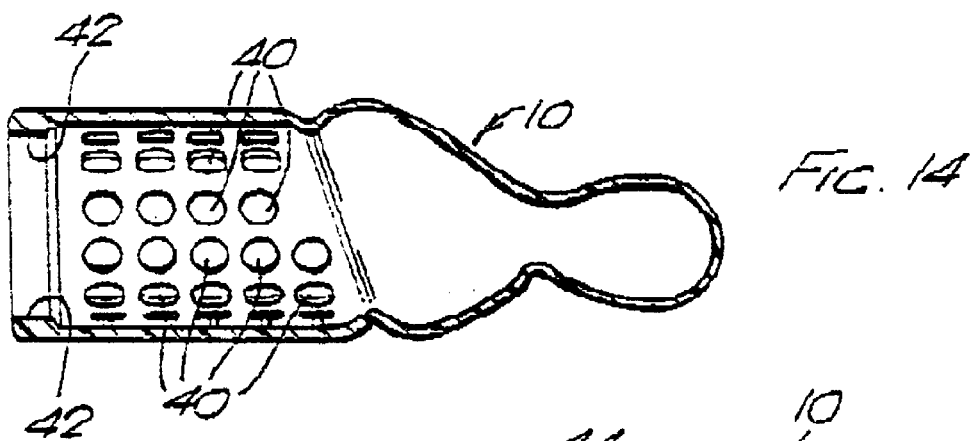
FIG. 14 is a side elevation in cross-section of the condom of the seventh embodiment; and, FIG. 15 is a side elevation in cross-section of the condom of the eighth embodiment.

In the seventh embodiment, shown in FIG. 14, the inner surface of the wide belt 12 is covered with a regular array of suckers 40. These will again help to hold the condom onto the penis. The diameter of the wide belt 12 is reduced at 42 behind the array of suckers 40. Thus, any semen which passes by the bead 36 and between the suckers 40 will be held within the condom.

Figure 15:
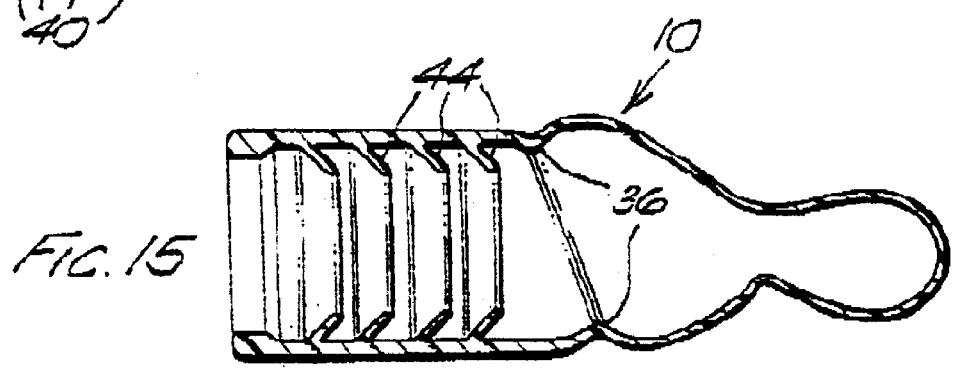

FIG. 15 shows yet another embodiment in which the inner surface of the wide belt 12 is provided with inwardly and forwardly directed circumferential ribs 44. The ribs 44 are resilient. If semen should reach the ribs 44. It will be directed behind the ribs which will reduce the chance of escape. Furthermore, if there is any force to pull the condom off the penis, the ribs 44 will act to resist that and in addition will straighten to increase the elastic force exerted by the ribs 44.

A number of different features are disclosed which may be used as described or in other combinations. For example adhesive may be used with the suckers in the seventh embodiment. Indeed the features of the last three embodiments may all be combined. In particular the feature of the use of a body of absorbent material 20 containing spermicide and/or prophylactic substances as in the second embodiment may be incorporated into any of the other embodiments.

The condom may be made of the conventional latex material or may be made out of any other known condom material such as the new polyurethane material which is very strong and can therefore be made very thin for enhanced sensation.

What is claimed is:

1. A male condom comprising a flexible sheath to receive the glans of the penis and a wide elastomeric belt connected to an open, rear edge of the sheath to lie around and grip the penis immediately behind the glans leaving the majority of that length of the penis which is behind the glans bare, the belt being so stiff that it cannot be rolled in use, the belt lying over the outside of the sheath in an initial position and being arranged to be manually reversed by a user when putting on the condom to lie to the rear of the sheath in a final position.

2. A condom as claimed in claim 1, wherein at least part of the axial length of the belt is lined with absorbent material to absorb and retain semen by forming a barrier to escape of semen.

3. A condom as claimed in claim 2, wherein the absorbent material is neoprene.

4. A condom as claimed in claim 2, wherein the absorbent material contains a contraceptive or prophylactic substance.

5. A condom as claimed in claim 1, wherein the belt is less than 60 mm wide.

6. A condom as claimed in claim 1, wherein the belt is less than 25 mm wide.

7. A condom as claimed in claim 1, wherein the belt is less than 12 mm wide.

8. A condom as claimed in claim 1, wherein the condom includes a teat which is resilient to resist collapse.

9. A condom as claimed in claim 1, wherein a portion of the belt which is to the rear when the belt is in the final position tapers to its rear edge.

10. A condom as claimed in claim 1, wherein the condom includes a further belt to lie around the base of the penis in use and at least one element connecting the two belts.

11. A condom as claimed in claim 10, wherein the or each element tapers from each belt to a central region of the element.

12. A condom as claimed in claim 10, wherein the condom includes a single element.

13. A condom as claimed in claim 10, wherein the condom includes two oppositely disposed elements.

14. A condom as claimed in claim 1, wherein the edge of the belt which is to the front when the belt is in the final position is shaped to the shape of the coronal sulcus.

15. A condom as claimed in claim 14, wherein the edge of the belt which is to the rear when the belt is in the final position is in a simple circle so that the belt is wider on the underside on the condom than on the top.

16. A condom as claimed in claim 1, wherein the edge of the belt which is to the front when the belt is in the final position is in a simple circle so that the belt is wider on the underside of the condom than on the top.

17. A condom as claimed in claim 1, wherein a restriction is provided at the edge of the belt which is to the front when the belt is in the final position to further improve the fit and to increase the elastic force in that region.

18. A condom as claimed in claim 1, wherein the part of the condom which is in contact with the shaft of the penis includes suckers to hold the condom onto the penis.

19. A male condom comprising a flexible sheath to receive the glans of the penis and a wide elastomeric belt connected to an open, rear edge of the sheath to lie around and grip the penis immediately behind the glans leaving the underside of the penis behind the belt bare, the belt being so stiff that it cannot be rolled in use, the belt lying over the outside of the sheath in an initial position and being arranged to be manually reversed by a user when putting on the condom to lie to the rear of the sheath in a final position.

20. A male condom comprising a flexible sheath to receive the glans of the penis and a wide elastomeric belt connected to an open, rear edge of the sheath to lie around and grip the penis immediately behind the glans leaving the majority of that length of the penis which is behind the glans bare, the belt lying over the outside of the sheath in an initial position and being arranged to lie to the rear of the sheath in a final position characterised in that at least part of the axial length of the belt is lined with absorbent material to absorb and retain semen by forming a barrier to escape of semen.

21. A condom as claimed in claim 2, 20, wherein the absorbent material is neoprene.

22. A condom as claimed in claim 20, wherein the absorbent material contains a contraceptive or prophylactic substance.

23. A male condom comprising a flexible sheath to receive the glans of the penis and a wide elastomeric belt connected to an open, rear edge of the sheath to lie around and grip the penis immediately behind the glans leaving the underside of the penis behind the belt bare, the belt lying over the outside of the sheath in an initial position and being arranged to lie to the rear of the sheath in a final position characterised in that at least part of the axial length of the belt is lined with absorbent material to absorb and retain semen by forming a barrier to escape of semen.

\* \* \* \* \*